United States Patent
Schroeder et al.

[11] Patent Number: 5,869,745
[45] Date of Patent: Feb. 9, 1999

[54] ULTRASONIC GAS PRESSURE MEASUREMENT FOR INFLATORS OF VEHICULAR AIRBAG SYSTEMS

[75] Inventors: David D. Schroeder, Ogden; Clark C. Strong; Marcus T. Clark, both of Kaysville, all of Utah; Marvin F. Fleming, Los Altos; Samuel Hersh, Danville, both of Calif.

[73] Assignee: Morton International, Inc., Chicago, Ill.

[21] Appl. No.: 771,451

[22] Filed: Dec. 20, 1996

[51] Int. Cl.$^6$ .................................................. G01N 29/02
[52] U.S. Cl. .............................. 73/31.04; 73/52; 73/629; 73/703; 73/708; 280/735; 280/736; 280/737; 280/741
[58] Field of Search .............................. 73/702, 703, 708, 73/756, 592, 597, 598, 627, 629, 645, 29.03, 31.04, 37, 40, 40.5 A, 49.2, 49.3, 52; 280/741, 737, 736, 735; 364/557, 558

[56] References Cited

U.S. PATENT DOCUMENTS

| | | | |
|---|---|---|---|
| 3,818,764 | 6/1974 | Wagner | 73/393 |
| 3,850,039 | 11/1974 | Brakebill | 73/420 |
| 3,942,381 | 3/1976 | Brown et al. | 73/398 R |
| 3,944,769 | 3/1976 | Wagner | 200/83 A |
| 3,977,252 | 8/1976 | Krylova et al. | 73/398 R |
| 4,009,616 | 3/1977 | Wonn | 73/398 R |
| 4,187,718 | 2/1980 | Shibasaki | 73/52 |
| 4,406,157 | 9/1983 | Miyahara et al. | 73/52 |
| 4,520,654 | 6/1985 | Terhune | 73/24 |
| 4,869,097 | 9/1989 | Tittman et al. | 73/52 |
| 4,938,066 | 7/1990 | Dorr | 73/597 |
| 5,016,474 | 5/1991 | Hazony et al. | 73/597 |
| 5,040,415 | 8/1991 | Barkhoudarian | 73/198 |
| 5,225,643 | 7/1993 | Marchant | 200/834 |
| 5,271,267 | 12/1993 | Baumoel | 73/54.41 |
| 5,351,527 | 10/1994 | Blackburn et al. | 73/52 |
| 5,433,476 | 7/1995 | Materna et al. | 280/736 |
| 5,504,288 | 4/1996 | Morin | 280/736 |
| 5,604,338 | 2/1997 | Paxton et al. | 200/83 N |

OTHER PUBLICATIONS

English Abstract of Soviet Union Patent No. 522427, Nov. 1976.
English Abstract of Soviet Union Patent No. 1413–456, Jul. 1988.
English Abstract of Soviet Union Patent No. 1462–129, Feb. 1989.

Primary Examiner—Hezron E. Williams
Assistant Examiner—Rose M. Miller
Attorney, Agent, or Firm—George W. Rauchfuss, Jr.

[57] ABSTRACT

An inflator for an airbag system has a target mounted in the pressurized gas contained in the inflator. An ultrasonic transducer is mounted on an external surface of the inflator in alignment with the target. The transducer generates and receives reflected ultrasonic signals from the target. The time-of-flight of the signals which are dependent on the gas pressure are used to determine the gas pressure in the inflator. Temperature compensation is provided by fabricating the target of bimetallic material which changes the spacing of the target from the transducer with temperature or providing a temperature sensitive element, e.g. a thermocouple to electrically provide temperature compensation.

10 Claims, 2 Drawing Sheets

ULTRASONIC GAS PRESSURE MEASUREMENT FOR INFLATORS OF VEHICULAR AIRBAG SYSTEMS

FIELD OF THE INVENTION

This invention relates to measuring gas pressure in an inflator for an airbag system, and more particularly to ultrasonic gas pressure measurement using a piezoelectric transducer for an airbag system.

BACKGROUND OF THE INVENTION

Vehicular airbag systems employ a stored deflated airbag which is adapted to be inflated on an undesirable predetermined impact of the vehicle with another object. An inflator, such as a hybrid, fluid filled, cold gas or similar type inflator, charged with an inflating fluid under pressure, such as an inert gas like argon, helium and the like or a mixture thereof, is caused to be discharged into the stored deflated airbag for inflating the same on the aforesaid undesirable predetermined impact. Accordingly, for the system to operate properly, the inflator pressure must not increase nor decrease beyond predetermined amounts, regardless of the temperature. Since the operating temperature of a vehicle varies, for example, from a vehicle parked outside in sub-freezing temperatures to one parked in the desert at elevated temperatures (greenhouse effect), the inflator pressure must be carefully monitored to maintain the integrity of the airbag systems.

One method of monitoring the pressure in an inflator is to use an ultrasonic transducer, e.g. U.S. Pat. Nos. 3,942,381 or 5,016,474, in which ultrasonic signals are supplied to an inflator container from the transducer and the time intervals between the application of such signals and the receipt of the return or echo signals from an opposing wall of the inflator are measured such as by time of flight (TOF) of the signals in order to determine various physical properties of the inflator container. One of the problems associated with such systems resides in the fact that inflator wall thickness has variable, not very tightly controlled, tolerances which adversely affect the TOF of the signals. Also, if one desires to operate the measuring system from an automotive electrical system restrictions on the available power from automotive electrical systems for driving the ultrasonic transducer would limit the distance which can be traversed by the ultrasonic waves to provide meaningful reflected signals needed to measure the gas pressure in the inflator. In addition, due to the strong influence of temperature on inflator pressure, some simple form of temperature compensation is required because any pressure measurement without such compensation would be meaningless due to the wide range of operating temperatures to which the measurement system can be subjected.

SUMMARY OF THE INVENTION

Accordingly, it is an object of this invention to provide a new and improved ultrasonic gas pressure measurement system for airbag inflators which is accurate and relatively simple to utilize.

Another object of this invention is to provide a new and improved ultrasonic gas pressure measurement of inflators for vehicle airbag systems which can operate using restricted power available from vehicle electrical systems.

Still another object of this invention is to provide a new and improved ultrasonic gas pressure measurement of inflators for vehicle airbag systems which can operate and provide accurate measurement over a wide temperature range.

In carrying out this invention in one illustrative embodiment thereof, an ultrasonic gas pressure measurement system is provided for measuring the gas pressure in an inflator of a vehicle airbag module. An inflator containing pressurized gas is provided which, upon activation, is adapted to be released into an airbag stored in an airbag module for inflating the airbag. The inflator contains a target surface therein and a temperature compensation means for compensating any changes in gas pressure due to temperature. An ultrasonic transducer means is mounted on the inflator in alignment with the target surface for transmitting ultrasonic signals to the target surface and detecting the reflected ultrasonic signals from the target surface, whereby the time-of-flight of the ultrasonic signals to and from the target through the pressurized gas is used to determine the pressure taking into account temperature changes. The target surface may comprise a bimetallic element for varying the distance of the target from the transducer in accordance with temperature, or a temperature sensitive detector, such as a thermocouple, may be mounted in the inflator to provide temperature compensation electrically.

BRIEF DESCRIPTION OF THE DRAWINGS

This invention together with further objects, aspects, features and advantages thereof, will be more clearly understood from the following description taken in connection with the accompanying drawings.

DESCRIPTION OF THE PREFERRED EMBODIMENTS

Figure 1:
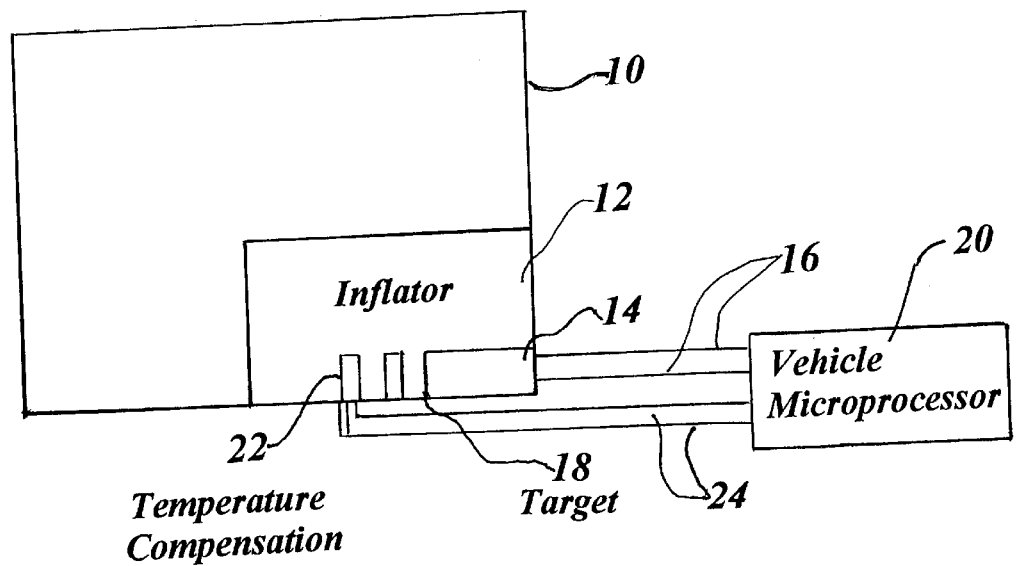
FIG. 1 is a diagrammatic block diagram of the ultrasonic gas pressure measurement system for inflators of vehicle airbag systems in accordance with the present invention.

Referring now to FIG. 1, an airbag module is referred to generally with the reference numeral 10. The module 10 has different sizes and shapes depending on whether the module is to be mounted in the steering column, instrument panel, door panel, etc. The module 10 contains a collapsed airbag (not shown) and an inflator 12 containing a pressurized or compressed gas 13, e.g. argon, helium, hybrid combination or the like, which is released into the collapsed airbag for the inflation thereof when the inflator 12 is actuated.

As pointed out previously, in order to insure the integrity of the airbag system, the pressurized gas in the inflator 12 must be maintained within a predetermined pressure range to insure the proper inflation of the airbag. Accordingly, the pressure in the present invention is monitored by a transducer 14, e.g. a piezoelectric crystal which is directly coupled to an exterior surface of the inflator 12. The transducer 14 is coupled by electrical leads 16, preferably to the vehicle diagnostic microprocessor 20, which also provide a power source to the transducer 14. The piezoelectric transducer 14 generates and transmits ultrasonic sound waves through the pressurized gas in the inflator 12 to a target surface 18 in the inflator 12. The target surface 18 then reflects the sound waves back through the pressurized gas to the transducer 14. The microprocessor 20 employs a clock (not shown) to measure the time-of-flight (TOF) of the ultrasonic signal through the pressurized gas. The TOF is dependent on the gas density (pressure) and as the density increases, the TOF decreases, and vice versa, which provides a convenient way to measure the gas pressure in the inflator. The TOF of the sound wave through a known gas medium is measured and can be directly correlated with either velocity, density or pressure. The measured value of the pressure by the transducer 14 can be compared to an acceptable pressure value or pressure value range stored in the microprocessor 20 to provide an alarm, a go, no-go signal or produce a pressure output. A microprocessor separate from the vehicle diagnostic system can be used for the measurement system if desired, but the incorporation and integration of the system into the diagnostic system of the vehicle is preferred.

Since the temperature of the pressurized gas has a significant effect on the velocity of the ultrasonic signals travelling through the gas, a temperature compensation means 22 must be provided in the inflator 12. One form of temperature compensation means 22 may be achieved electrically by a thermocouple positioned in the area of the pressurized gas in the inflator 12. The thermocouple is coupled by electrical leads 24 to the microprocessor 20 which factors out temperature effects electronically in known fashion. Other forms of temperature sensitive elements, such as a thermistor, could be used in place of the thermocouple to provide an electrical temperature compensation means.

Figure 2:
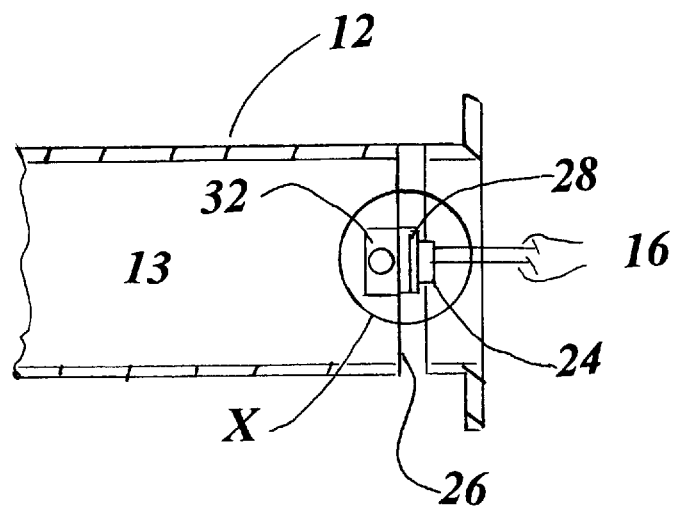
FIG. 2 is a partial cross-sectional view of an inflator in accordance with one aspect of the present invention.
Figure 3:
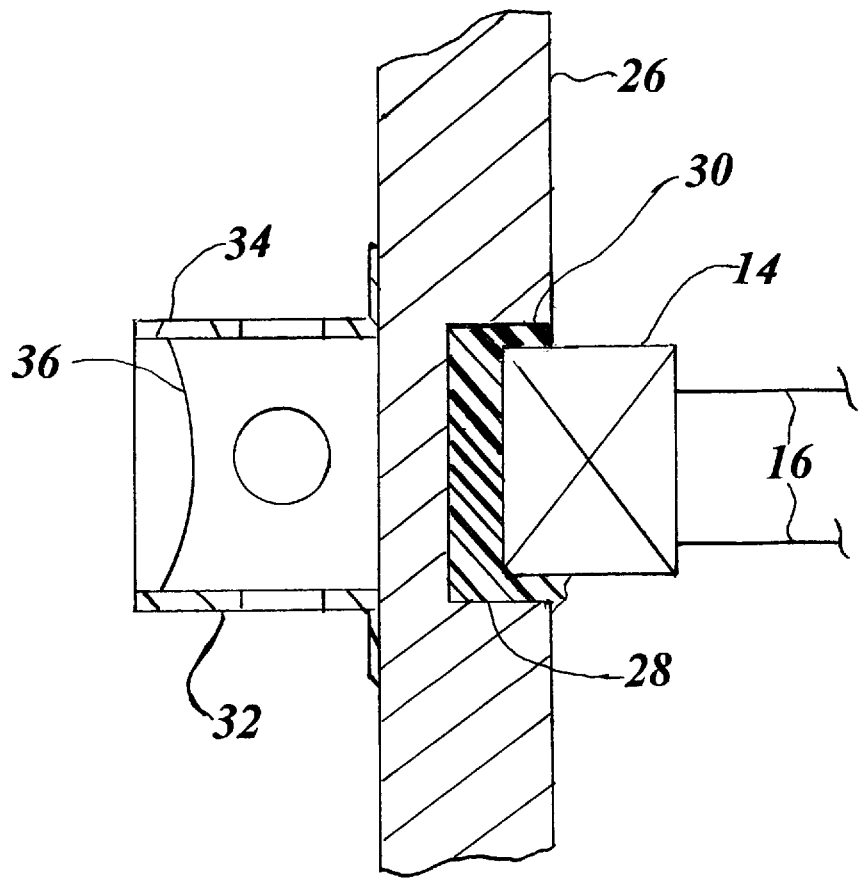
FIG. 3 is an enlarged view of the encircled area "X" of the inflator shown in FIG. 2.

Referring now to FIGS. 2 and 3 which show detailed views of a preferred form of the invention, the inflator 12, filled with pressurized argon/helium gas 13, contains an end plug 26, e.g. plain carbon steel, having a central recess 28 therein. The piezoelectric ultrasonic transducer 14 (e.g. 2.25 MHZ; 0.375 inch diameter, highly damped, KB-A, 33487 typical) is mounted in the recess 28 by a couplant 30, e.g. a damping material such as epoxy containing colloidal alumina. The transducer 14 may be fixedly mounted on the outer surface of the inflator 12, but the recessed mounting is preferred in order to accurately directly align the transducer 14 with a target 36 mounted in the pressurized gas in the inflator. In addition, excellent coupling is more readily assured using a recessed mounting. Note that whether the transducer 14 is mounted on the surface or in a recess 28 in the inflator 12, the ultrasonic system is externally applied to the inflator and is therefore non-intrusive, as distinguished from those measuring systems which require a sensor to be in intimate contact with the gas environment. Intimate contact measuring systems require a through opening into the inflator which involves additional expense and requires leak testing.

In accordance with one aspect of the invention, the end plug 26 carries a target stand 32 having an annular recess 34 therein, which has a target 36 mounted therein in alignment with the transducer 14. Using the target 36 instead of measuring from the inflator wall inside diameter permits the mounting of a temperature compensator, i.e., a bimetallic disk, as the target to provide a reflector for the ultrasonic signal as well as a temperature compensator. The voltage available from the vehicle for airbag inflator pressure measurement purposes is low so the distance between the transducer 14 and the target 36 can be reduced or kept small in order to obtain a measurable reflected or echo signal. In addition, the distance between the transducer and the target must be consistently the same, which can be more tightly controlled by fabricating a target with more tightly controlled tolerances than with respect to tolerances of wall thickness and height of the rebound surface. Such latter tolerances cannot be so tightly controlled in making containers such as inflators, where the contours of the inside surfaces and the thickness of the inflator walls are not easily precisely controlled.

The bimetallic target 36 which moves away from and toward the transducer 14 as the temperature of the pressurized gas in the inflator 12 increases or decreases, respectively, provides a longer or shorter TOF path for the ultrasonic waves from the transducer 16, thereby compensating for an increase or decrease in the velocity of the sound waves due to temperature changes. One form of bimetallic material which may be employed is Polymet 703-1 manufactured by Polymetallurgical, Attleboro, Mass. The bimetallic disk target 36 comprises two alloy foils bonded together. The first alloy makes up 55% of the thickness and contains 70% copper and 30% zinc. The second alloy is 36% nickel and the remainder iron (commonly called Invar). In an illustrative example, the target 36 is 0.75 inches in diameter and 0.00625 inches thick. The target disk 36 is designed to bow inward toward the ultrasonic source 16 (see FIG. 3) so that the ultrasonic signal consistently strikes the center of the target disk rather than the edges.

Accordingly, the embodiment shown in FIG. 3 of mounting the transducer 14 as well as the target 36 on the inflator end plug 26 provides alignment and spacing advantages as well as advantages in construction of the inflator 12. The spacing and tolerances of the target may be tightly controlled to provide more accurate measurement while limiting the amount of power required for the gas pressure measurement. Therefore, the target structure 18 in a form other than a bimetallic disk would be advantageous and could be used in combination with a temperature sensitive element such as a separate thermocouple as shown in FIG. 1.

The present ultrasonic gas pressure measurement system provides a non-intrusive method of measuring the gas pressure of the inflator without requiring transducer contact with the pressurized gas in the container. The pressure measurement system of this invention can be integrated in the existing diagnostic system of the vehicle and can monitor the gas pressure of an inflator over a wide temperature range using low voltages which do not tax the vehicle's electrical system.

Since other changes and modifications varied to fit particular operating requirements and environments will be apparent to those skilled in the art, the invention is not considered limited to the examples chosen for purposes of illustration, and includes all changes and modifications which do not constitute a departure from the true spirit and scope of this invention as claimed in the following claims and equivalents thereto.

We claim:

1. An ultrasonic gas pressure measurement system for measuring gas pressure in an inflator of a vehicle airbag module comprising:

an inflator containing pressurized gas which, on the activation of said inflator, is adapted to be released into an airbag stored in an airbag module for inflating the airbag, said inflator having a target surface therein, a temperature compensation means mounted in said inflator for compensating for any changes in gas pressure due to temperature, an ultrasonic transducer means mounted on said inflator in alignment with said target surface for transmitting ultrasonic signals to said target surface and detecting reflected ultrasonic signals from said target surface, wherein said temperature compensation means comprises a bimetallic member which forms said target surface in said inflator whereby changes in temperature of said pressurized gas in said inflator changes the distance between said target surface and said ultrasonic transducer means, thereby varying the time-of-flight of said ultrasonic signals in said inflator in accordance with temperature to compensate for changes in temperature, whereby time-of-flight of the ultrasonic signals to and from the target through the pressurized gas in the inflator is used to determine the gas pressure in the inflator taking into account the temperature of the pressurized gas.

2. The ultrasonic gas measurement system as claimed in claim 1 wherein the target surface is mounted within the pressurized gas in said inflator.

3. The ultrasonic gas pressure measurement system as claimed in claim 1 wherein said ultrasonic transducer is coupled to a vehicle diagnostic microprocessor for the vehicle in which the measurement system is employed.

4. The ultrasonic gas measurement system as claimed in claim 1 wherein said bimetallic member comprises first and second alloy foils bonded together.

5. The ultrasonic gas measurement system as claimed in claim 4 wherein the first alloy foil contains copper and zinc and the second alloy foil comprises nickel and iron.

6. An ultrasonic gas pressure measurement system for measuring gas pressure in an inflator of a vehicle airbag module comprising:

an inflator containing pressurized gas, a target mounted in said pressurized gas in said inflator, an ultrasonic transducer mounted on an outer surface of said inflator in alignment with said target for transmitting and receiving ultrasonic signals from said target whereby time-of-flight of said ultrasonic signals is used to determine the gas pressure in said inflator, temperature compensation means mounted in said pressurized gas in said inflator for providing temperature compensation for change in gas pressure based on temperature changes of the gas in the inflator, wherein said temperature compensation means comprises said target which comprises a bimetallic disk whose distance from said ultrasonic transducer is varied in accordance with temperature, thereby varying the time-of-flight of said ultrasonic signals to provide said temperature compensation for said gas pressure measurement, and a microprocessor coupled to said ultrasonic transducer for measuring and monitoring the gas pressure in said inflator.

7. The ultrasonic gas measurement system as claimed in claim 6 wherein the bimetallic disk comprises first and second alloy foils bonded together, the first alloy foil contains copper and zinc and the second alloy foil comprises nickel and iron.

8. The gas pressure measurement system as claimed in claim 6 wherein said inflator has an end plug, said target and said ultrasonic transducer being mounted in alignment on said end plug.

9. The gas pressure measurement system as claimed in claim 8 wherein said end plug of said inflator is recessed and said ultrasonic transducer is mounted in the recessed end plug.

10. The ultrasonic gas measurement system as claimed in claim 9 wherein the bimetallic disk comprises first and secnd alloy foils bonded together, the first alloy foil contains copper and zinc and the second alloy foil comprises nickel and iron.

* * * * *